US006643016B2

(12) United States Patent
Garver et al.

(10) Patent No.: US 6,643,016 B2
(45) Date of Patent: Nov. 4, 2003

(54) MULTIPLE PATHLENGTH SPECTROPHOTOMETER

(75) Inventors: Theodore M. Garver, Edmonton (CA); David G. Jenkins, Canyon Country, CA (US); Andrew Riser, Newbury, OH (US)

(73) Assignee: Alberta Research Council Inc., Edmonton (CA)

( * ) Notice: Subject to any disclaimer, the term of this patent is extended or adjusted under 35 U.S.C. 154(b) by 148 days.

(21) Appl. No.: 09/846,232

(22) Filed: May 2, 2001

(65) Prior Publication Data

US 2001/0055115 A1 Dec. 27, 2001

(30) Foreign Application Priority Data

Jun. 27, 2000 (CA) ............................................. 2312501

(51) Int. Cl.[7] ................................ G01J 3/30; G01J 3/18
(52) U.S. Cl. ....................... 356/320; 356/312; 356/345
(58) Field of Search ................................ 356/246, 326, 356/328, 419, 435, 320, 312, 345

(56) References Cited

U.S. PATENT DOCUMENTS

| | | | | |
|---|---|---|---|---|
| 3,532,429 A | * | 10/1970 | Hughes et al. ............... 356/320 |
| 3,985,441 A | | 10/1976 | Schoeffel et al. .............. 356/88 |
| 4,030,828 A | | 6/1977 | Sonobe et al. ................ 356/96 |
| 4,298,797 A | | 11/1981 | Bernard et al. .............. 250/372 |
| 4,571,074 A | | 2/1986 | Thevenon ..................... 356/51 |
| 4,779,959 A | | 10/1988 | Saunders .................... 359/237 |
| 4,786,171 A | | 11/1988 | LeFebre et al. .............. 356/326 |
| 4,958,928 A | | 9/1990 | Kuderer ....................... 356/328 |
| 5,017,785 A | * | 5/1991 | Rasanen ....................... 250/345 |
| 5,018,856 A | * | 5/1991 | Harnly et al. ................ 356/312 |
| 5,114,498 A | | 5/1992 | Okamoto et al. ............ 136/258 |
| 5,116,123 A | | 5/1992 | Kuderer ....................... 356/326 |
| 5,168,367 A | | 12/1992 | O'Rourke et al. ........... 356/246 |
| 5,173,748 A | | 12/1992 | Bilhorn ........................ 356/328 |
| 5,218,473 A | | 6/1993 | Seddon et al. ............... 359/589 |
| 5,242,602 A | | 9/1993 | Richardson et al. ......... 210/745 |
| 5,268,736 A | | 12/1993 | Prather ......................... 356/246 |
| 5,408,326 A | | 4/1995 | Wang ........................... 356/410 |
| 5,410,431 A | | 4/1995 | Southwell .................... 359/580 |
| 5,602,647 A | | 2/1997 | Xu et al. ...................... 356/435 |
| 5,616,214 A | | 4/1997 | Leclerc ......................... 162/49 |
| 5,641,966 A | | 6/1997 | Karlberg et al. ............. 258/323 |
| 5,773,828 A | | 6/1998 | Akiyama et al. ............ 250/345 |
| 5,842,150 A | | 11/1998 | Renberg et al. ............... 702/23 |
| 5,876,674 A | | 3/1999 | Dosoretz et al. .............. 422/91 |
| 6,023,065 A | | 2/2000 | Garver, Jr. .................... 250/372 |
| 6,057,925 A | | 5/2000 | Anthon ......................... 356/419 |

* cited by examiner

*Primary Examiner*—Thong Nguyen
(74) *Attorney, Agent, or Firm*—Lacasse & Associate

(57) ABSTRACT

A spectrometer or multiple wavelength absorbance detection method and apparatus providing improved accuracy for an array of measurements at different wavelengths. The spectrometer utilizes a multiple wavelength illumination system with an array of independent detectors with different pathlength cells, where each cell is illuminated with predominately monochromatic light after separation by a light dispersing element. Each sample cell has an optical pathlength, optics and photodetection device that are optimized for its particular wavelength to accurately measure absorbance through an expected substance.

34 Claims, 8 Drawing Sheets

MULTIPLE PATHLENGTH SPECTROPHOTOMETER

FIELD OF THE INVENTION

The present invention relates generally to ultraviolet-visible spectrophotometers and absorbance detectors, and, more particularly, to a novel method and accompanying apparatus for extending the linear dynamic range of such detectors by separation of incident light before a series of variable path length cells.

DESCRIPTION OF THE PRIOR ART

A widely used method for monitoring various characteristics of a sample of interest relies upon obtaining accurate measurements of light absorption by the sample. Such measurements are commonly performed as a function of wavelength. For example, the concentration of a solute in a solution can be determined quantitatively by comparing a measured intensity of light transmitted through a sample to a reference light intensity, or alternatively the qualitative identity of the solute may be inferred by considering the various specific wavelengths of light that are absorbed by the sample. In many laboratory and industrial uses of spectrometry the relative intensities or absorbance values at selected wavelengths are needed and the analysis of every point in a complete spectrum is not necessary. Often the point of an analysis is to derive a concentration of one or more components that absorb light. In other cases, points from the absorbance spectrum may be used to define a quality indicator using regression or chemometric techniques. These quantitative analysis applications of spectrometry may require the use of absorbance or intensity values obtained at widely different wavelengths with absorption or emission values that vary substantially. A spectrometer is normally configured to provide the highest accuracy at one wavelength, causing measurements at other wavelengths to be less accurate.

Many spectrometers are available that use a single path length with a single light source and many detectors including photodiode arrays such as Kuderer, U.S. Pat. No. 4,958,928, Kuderer, U.S. Pat. No. 5,116,123, and Bilhorn, U.S. Pat. No. 5,173,748. These systems typically use a monochrometer between the sample and the detector to separate out a single wavelength for measuring absorbance. By scanning the monochrometer, absorbance can be measured at different wavelengths, but not simultaneously. Optical Coating Laboratories, however, has disclosed a miniature spectrometer with optical filters instead of a monochrometer as disclosed in Anthon, U.S. Pat. No. 6,057,925. In Wang, U.S. Pat. No. 5,408,326, a two-wavelength absorbance detector was disclosed that uses two independent light sources and a single sample pathlength to measure two values simultaneously. Additionally, prior art multiple wavelength systems such as the Ocean Optics PC2000 unit or the CVI SM200S unit extract substantial information as a function of wavelength simultaneously, but resolution is limited because intensity information is gathered by 12-bit or 16-bit count CCD elements. CCD based systems inherently have limited dynamic range due to the limits of charge accumulation in the device well and the analogue-to-digital conversion resolution. CCD elements with a 12-bit well depth or a 16-bit well (deep well) depth are available, which provide 4096 and 65536 increments of intensity, respectively. In addition to CCD arrays, diode array instruments can be used, but both generally require significant processor overhead to complete the measurement. Photodiodes or photomultipliers provide much higher, sensitivity, dynamic range and linearity compared to CCD elements. This is discussed in Perkini Elmer Technical Document, Choosing the Detector for your Unique Light Sensing Application, by Larry Godfrey and is available on the World Wide Web at http://opto.perkinelmer.com/library/papers/tp4.htm.

Certainly in industrial measurement and control it is often necessary to reduce a group of measurements at different wavelengths to one or two easy to understand and control process parameters. In fact, other characteristics of the sample of interest may be investigated by performing more complex analyses of the absorbance data. Several patents have addressed methods for extracting performance indicators from absorbance data. For example, Richardson et al., U.S. Pat. No. 5,242,602, teach the use of chemometrics or linear regression techniques with multiple ultraviolet-visible absorbance measurements to derive water treatment performance indicators. International Patent Application WO 96/12183 discloses a method of determining quality parameters and the organic content in pulp and paper mill effluents by applying chemometric methods. In the method disclosed in WO 96/12183 the chemometric algorithms are applied directly to the spectroscopic data. The spectra are subjected to data treatment using values from several discrete wavelengths from each particular spectrum. U.S. Pat. No. 6,023,065, issued to Garver, discloses a method for monitoring and controlling a characteristic of process waters that uses at least two measurements of ultraviolet light absorption to construct a ratio for computing an empirical value of the characteristic of the effluent or process. Garver taught that the use of at least one absorbance ratio to derive a performance indicator improved the information extraction from the absorbance spectrum by providing a means to model non-linear processes and decouple covariant absorbance data. Feedback control is used for adjusting feed input components in accordance with the computed empirical value of the characteristic such that a target measurement of the characteristic is obtained while the excess amount of the input component is kept to a minimum.

According to the method disclosed in U.S. Pat. No. 6,023,065, accurate real-time absorbance data for up to eight different predetermined wavelengths of ultraviolet light are required to obtain empirical values for a plurality of effluent characteristics including: pulp final target brightness; yellowness; residual peroxide; brightness efficiency, yellowness efficiency; and delignification efficiency. For this reason, it will be appreciated that single-wavelength units do not provide sufficient information to determine multiple performance indicators that are dependent on more than one input. Furthermore, the generation of ultraviolet-visible absorbance ratios can multiply signal noise when the absorbance value is in the denominator of the ratio. A very low absorbance at a long wavelength, for example, may be used in a denominator to represent color and an intense absorbance at a short wavelength may be used to represent a bleaching agent such as hydrogen peroxide, for example. In this case the ratio of high absorbance to low absorbance is substantially less accurate than the high absorbance value or the low absorbance value. For example, if the actual ratio is $A_{230}/A_{350}$, and the error is expressed as $err_{230}$ and $err_{350}$ the measured ratio=$[A_{230} \pm err_{230}]/[A_{350} \pm err_{350}]$. In a simplified e spectrometer error is 0.01 absorbance units at all wavelengths and absorbance values and absorbance measurements were 1.000 at 230 nm and 0.08 at 350 then the error at 230 nm is 1%. the error at 350 nm is 12.5% and the error in the ratio is ~15%. This simplified example highlights the need for highly accurate absorbance values at different wavelengths when functions with division of absorbance values are used. In practice, different types of accuracy, resolution, and linearity increase error at both high and low absorbance values. An absorbance detection system is typically optimized for measurements between 0.3 and 0.9 absorbance units.

In general, measurements of a quantitative nature entail a prior calibration of the instrument response using at least two different calibration standards of the sample of interest to prepare an absorption curve. Preferably, the prior calibration of the instrument response is such that the light absorption by the fluid sample tends toward an amount of absorption approximately central to an approximately linearly varying region of the absorption curve for the sample at a predetermined wavelength of light. Unfortunately, prior art ultraviolet-visible spectrophotometers are optimised for providing an accurate measurement of light absorption by a sample for only a narrow range of wavelengths of the electromagnetic spectrum. An absorbance measurement using light from other than the optimal wavelength range is obtained with reduced accuracy due to the limited linear dynamic range of the instrument and the decreased digital resolution.

Absorbance is defined as:

$$A = -\log(I/I_o) = \epsilon_\lambda c l \quad (1)$$

where:

A = the absorbance in absorbance units, $I_o$ = the quantity of incident light provided by the source, I = the quantity of light transmitted through the sample and to the light detector, $\epsilon_\lambda$ = the wavelength dependent molar extinction coefficient of the sample, c = the sample concentration in moles/liter, and l = the path length of the measurement cell in cm, wherein the wavelength dependent molar extinction coefficient $\epsilon_\lambda$ of the sample can vary substantially with wavelength. As a result of the wavelength dependence of $\epsilon_\lambda$, single path-length spectrophotometers lead to a dynamic range problem when performing absorbance measurements at a plurality of different wavelengths. Specifically, the instrument response is calibrated to measure accurately the absorbance of light at a first predetermined wavelength $\lambda(1)$ such that the product $\epsilon_{\lambda(1)} c l$ from Equation (1) yields an absorbance value that is approximately equal to the median value of the highest calibration standard concentration and the lowest calibration standard concentration. Unfortunately, the molar extinction coefficient $\epsilon_{\lambda(2)}$ of the sample at a second predetermined wavelength of light $\lambda(2)$ is likely to be substantially different, and thus the product $\epsilon_{\lambda(2)} c l$ will correspond more closely to one of the highest calibration standard concentration or the lowest calibration standard concentration. Alternatively, the product $\epsilon_{\lambda(2)} c l$ is beyond the range of absorbance values for which the instrument response has been calibrated. Measurements of light absorption performed at high absorbance or at low absorbance are more statistically prone to errors and insufficient digital resolution. These arguments may be applied to any measurement of light extinction, not just light absorbance. Light extinction (attenuation) is a complicated function of the light absorption of a liquid; the light absorption of particles, if present; the light emission by fluorescence from dissolved or colloidal components; and the scattering that deflects light away from or towards the detector.

A solution is to vary the path-length through the sample for light of each different predetermined wavelength, to optimize the accuracy of the absorbance measurement at each predetermined wavelength. Variable path-length instruments are known in the art. For instance, LeFebre et al., U.S. Pat. No. 4,786,171, O'Rourke et al., U.S. Pat. No. 5,168,367 and Prather, U.S. Pat. No. 5,268,736. discloses devices that use one of a servomechanism or a linear stepper motor to vary the path length of light through a sample. Unfortunately, these devices are not well suited for obtaining simultaneous absorbance measurements at a plurality of different wavelengths, each measurement requiring a unique path length. The concurrent measurement of light absorption at a plurality of different wavelengths is crucial for on-line analysis of effluents, such as in the pulp and paper manufacturing industry, where process feed back control is required to maintain a desired characteristic of the product stream. In addition, the path length variation of the prior art systems is based upon a mechanical adjustment to the length of the sample cell, which raises a concern about the accuracy and reproducibility of the mechanical mechanism during extended periods of operation.

Xu et al., U.S. Pat. No. 5,602,647 disclosed a different variable path-length instrument that employs a wedge-shaped sample cell having a cross-sectional form of a right-angle triangle. A collimated beam of monochromatic laser light is launched into the sample cell through a light transmissive surface that is normal to the direction of propagation of the light. The light exits through a second light transmissive surface that is equivalent to the hypotenuse of the right-angle triangle. Thus, the light exiting the cell travels a different optical distance in dependence upon the point at which the light originally entered the cell. A multiplicity of photo detectors is arranged parallel to the exit surface of the cell for detecting the intensities of the rays of transmitted light, having traveled different optical path lengths through the sample, at positions of an equal distance from the cell. Alternatively, the sample cell is constructed with a staircase shape such that the light transmissive entrance surface is disposed parallel to a plurality of smaller light transmissive exit surfaces. The optical path length through the sample cell is measured along a line normal to the light transmissive entrance surface and normal to the specific light transmissive exit surface through which the light beam exits. Of course, monochromatic laser light is used and thus obtaining absorbance measurements at a plurality of different predetermined wavelengths involves performing a series of individual absorbance measurements, one absorbance measurement at each different predetermined wavelength. In addition, the use of optical elements for focusing the laser light and for enlarging the diameter of the laser beam larger than that of the original complicates further the design of such an apparatus.

In another embodiment of the invention disclosed in U.S. Pat. No. 5,602,647, a rectangular shaped sample cell with a fixed first light transmissive surface and with a moveable second other light transmissive surface is described. A source projects light toward the sample cell, where the path length of the sample cell may be varied by moving the moveable second other light transmissive surface in a direction parallel to the direction of propagation of the light. It is further disclosed that the source may be one of a tunable laser for providing monochromatic laser light or a lamp for providing polychromatic light. Unfortunately, in a case where a lamp for providing polychromatic light is used, a spectral disk including a plurality of individually selectable different filters, which transmit only light of their corresponding wavelengths, is required. Then, the light derived from the lamp is formed into collimated light by a convex lens, where only light of a selected wavelength is incident upon the cell, which is in a state of only one optical path length. The wavelength resolution of this design is limited by the light filter.

Still another variable path-length instrument is described in U.S. Pat. No. 5,773,828, issued to Akiyama et al. The device comprises a plurality of measuring cells, including a case where the cells are different in length from each other, that communicate sequentially with each other through a communication part to form a single gas path. The arrangement of a plurality of sample cells along a single gas path makes the device well suited for its intended use for the concurrent quantitative analysis of multi-components of a gaseous sample at a high accuracy. Advantageously, each measuring cell provides a fixed optical path length that is appropriate for measuring light absorption by one specific component of the plurality of components of the gaseous sample. It is a drawback of the apparatus that a complicated arrangement of cut-on filters and band-pass filters are used for spectrally separating the infrared radiation provided by the source and for directing the separated light, consisting of relatively broad ranges of wavelengths, along the various optical paths. The use of multiple cut-on filters for wavelength selection is an inefficient process in general. More specifically, the efficiency of band-pass filters in the ultraviolet region is low, typically approximately 12%, and the separation of light into ranges narrower than the order of tens of nanometers is unachievable. In the ultraviolet region of the electromagnetic spectrum $\epsilon_\lambda$ can vary substantially even over a ten to twenty nanometer wavelength range. Hence, the use of cut-on and band-pass filters for separating ultraviolet light is other than a viable option if high accuracy absorbance measurements are desired, and one of skill in the art would not make reference to it.

On-line monitoring of a process effluent, for providing real-time analysis of effluent characteristics to a feed back system controller, is a critical aspect of process control in the environmental monitoring, effluent treatment, food processing, textile and pulp and paper manufacturing. Methods deriving multiple concentrations or performance indicators such as those disclosed in U.S. Pat. Nos. 5,242,602, 5,842,150, 5,641,966, 6,023,065, 5,616,214 require accurate measurements at different wavelengths for optimal information extraction. It is a limitation of the prior art systems that a measurement of an absorbance of substantially monochromatic ultraviolet light must be performed as a series of separate measurements, one measurement required for each different predetermined wavelength of light. Of course, the prior art systems require a finite length of time to obtain such a series of absorbance measurements, said length of time representing an unavoidable delay before an action is taken in response to the changing conditions of the effluent. The ability to make a rapid, accurate measurement is of considerable advantage in short time frame situations. For example, during chromatographic separation of an analyte a single component may pass a detector in less than 1 second. During the initial phase of a rapid chemical reaction, the changes are very rapid and sequential measurements potentially will fail to accurately quantify a changing chemical composition. The inability to rapidly make many measurements that are used for optimization and control may lead to inefficient operation. Potential losses to the company include: lost productivity and high capital costs associated with replacing damaged machinery; lower revenues and higher production costs due to excessive production of off-grade product; and, cleanup costs, fines and poor public image following the release of unacceptably high levels of toxins into the environment.

It would be advantageous to provide an apparatus for obtaining concurrently an accurate, on-line measurement of the quantity of light absorbed by a product stream or effluent, at each of a plurality of different predetermined wavelengths where the illumination and detection at each wavelength is optimized for accuracy.

OBJECT OF THE INVENTION

In order to overcome these and other limitations of the prior art, it is an object of the invention to provide an apparatus for obtaining simultaneously on-line measurement of the quantity of light absorbed by a product stream or effluent at each of a plurality of different predetermined wavelengths.

SUMMARY OF THE INVENTION

According to the present invention a portion of fluid matter is diverted through a series of sequentially connected measuring cells, the fluid contained by each measuring cell having substantially a same composition. Each measuring cell is disposed along a separate optical path for measuring the quantity of approximately monochromatic light absorbed by the product stream. The optical path length of each measuring cell is unique, being determined in dependence upon the wavelength of light propagating through each different measuring cell. Further advantageously the configuration of the apparatus supports the use of a plurality of light detectors, one light detector required for each separate optical path. Thus, the wavelength variation of the reference spectrum may be minimized using variable integration times at each independent light detector. The configuration of said apparatus solves several problems related to achieving high accuracy ultraviolet-visible absorption data from a process effluent, which are not adequately addressed by the prior art systems.

In accordance with an embodiment of the current invention, there is provided a method of measuring light absorption by a fluid sample comprising the steps of:

a) providing polychromatic light along an initial optical path;

b) dispersing the polychromatic light in dependence upon wavelength:
   to direct light at a first predetermined wavelength along a first optical path having a first path length through the fluid sample; and,
   direct light at a second other predetermined wavelength along a second other optical path having a second other path length through the fluid sample;

c) detecting an intensity of light at the first predetermined wavelength after it has propagated the first optical path length through the fluid sample using a first light detector disposed within the first optical path and supporting a first range of detected values; and, d) detecting an intensity of light at the second other predetermined wavelength after it has propagated the second optical path length through the fluid sample using a second other light detector disposed within the second other optical path and supporting a second range of detected values, wherein the first path length is selected in dependence upon the first wavelength and the fluid sample such that a detected first value is within a portion of the first range wherein substantial variations in optical intensity result in substantial changes in the first value, and, wherein the second path length is selected in dependence upon the second other wavelength and the fluid sample such that a detected second value is within a portion of the second range wherein substantial variations in optical intensity result in substantial changes in the second value, and, wherein the first light detector is angularly disposed along an arc section of a Rowland circle in dependence upon the first wavelength of light and the second other light detector is angularly disposed along a same arc section of a same Rowland circle in dependence upon the second other wavelength of light.

In accordance with another embodiment of the current invention, there is provided a method of measuring light absorption by a fluid sample including a light absorbing species comprising the steps of:

a) providing polychromatic light along an initial optical path;

b) dispersing the polychromatic light in dependence upon wavelength:
   to direct light at a first predetermined wavelength along a first optical path having a first path length through the fluid sample; and,
   to direct light at a second other predetermined wavelength along a second other optical path having a second other path length through the fluid sample;

c) detecting an intensity of light at the first predetermined wavelength after it has propagated the first optical path length through the fluid sample using a first light detector disposed within the first optical path and supporting a first range of detected values; and, d) detecting an intensity of light at the second other predetermined wavelength after it has propagated the second optical path length through the fluid sample using a second other light detector disposed within the second other optical path and supporting a second other range of detected values, wherein the first path length is selected in dependence upon the first wavelength and the fluid sample such that a detected first value is within a portion of the first range wherein substantial variations in optical intensity result in substantial changes in the first value, and, wherein the second path length is selected in dependence upon the second other wavelength and the fluid sample such that a detected second value is within a portion of the second range wherein substantial variations in optical intensity result in substantial changes in the second value, and, In accordance with yet another embodiment of the current invention, there is provided an apparatus for measuring light absorption by a fluid sample comprising:

at least a light source for providing polychromatic light along an initial optical path;

a light separating element disposed within the initial optical path for receiving the polychromatic light from the at least a light source and for dispersing the polychromatic light in dependence upon wavelength to direct light at each of a plurality of different predetermined wavelengths along one of a plurality of different secondary optical paths, including a signal at a first predetermined wavelength of light propagating along a first secondary optical path and a signal at a second other predetermined wavelength of light propagating along a second other secondary optical path;

a first channel detector disposed within the first secondary optical path comprising:

a) a first sample cell for containing a fluid sample within a containing portion thereof and having at least a light transmissive endface; and, b) a first light detector disposed for receiving light at the first predetermined wavelength from one of the at least a light transmissive endface of the first sample cell, light at the first predetermined wavelength propagating a first optical path length through the containing portion of the first sample cell;

a second channel detector disposed within the second other secondary optical path comprising:

a) a second other sample cell for containing a fluid sample within a containing portion thereof and having at least a light transmissive endface; and, b) a second other light detector disposed for receiving light from one of the at least a light transmissive endface of the second other sample cell, light at the second other predetermined wavelength propagating a second different optical path length through the containing portion of the second other sample cell;

wherein the light separating element defines a Rowland circle, the first channel detector and the second other channel detector being angularly disposed along an arc section of the Rowland circle in dependence upon the first predetermined wavelength of light and the second other predetermined wavelength of light, respectively.

In accordance with yet another embodiment of the current invention, there is provided an apparatus for measuring light absorption by a fluid sample comprising:

at least a light source for providing polychromatic light along an initial optical path;

a dispersive element disposed within the initial optical path for receiving the polychromatic light from the at least a light source and for dispersing the polychromatic light in dependence upon wavelength to direct light at each of a plurality of different predetermined wavelengths along one of a plurality of different secondary optical paths, including a signal at a first predetermined wavelength of light propagating along a first secondary optical path and a signal at a second other predetermined wavelength of light propagating along a second other secondary optical path;

a same sample cell disposed within the first secondary optical path and the second other secondary optical path for containing a same fluid sample within a same containing portion thereof and having at least a light transmissive endface, the at least a sample cell being shaped such that:

light at the first predetermined wavelength propagates along a first optical path length through the same containing portion of the same sample cell; and, light at the second other predetermined wavelength propagates along a second other optical path length through the same containing portion of the same sample cell, a first light detector disposed for receiving light at the first predetermined wavelength from one of the at least a light transmissive endface of the same sample cell; and, a second other light detector disposed for receiving light at the second other predetermined wavelength from one of the at least a light transmissive endface of the same sample cell, wherein the dispersive element defines a Rowland circle, the first light detector and the second other light detector being angularly disposed along an arc section of the Rowland circle in dependence upon the first predetermined wavelength of light and the second other predetermined wavelength.

Although many prior art spectrometer designs are known, a system including a plurality of sample cells, each sample cell for providing a different optical pathlength through a substantially same fluid sample, and wherein each sample cell is disposed within a different optical path so as to receive substantially monochromatic light at one of a plurality different predetermined wavelengths, and wherein further there is provided within each optical path an individual light detector, the light detector being optimised for measuring a light absorbance by the fluid sample at the wavelength of light that is directed along that optical path, is unknown.

DETAILED DESCRIPTION OF THE INVENTION

While the description of the preferred embodiment of the invention disclosed herein is a specific example where sample absorption characteristics are desired for eight different predetermined wavelengths of the ultraviolet-visible light spectrum, numerous modifications of the invention to allow the study of any number of different predetermined wavelengths over a different spectrum are possible by modifications of the types of light sources, dispersing elements or location and/or number of slits without departing substantially from the teachings of the invention as set forth below.

For many applications it is essential that the most accurate measurement of the light absorption by a sample be obtained. The accuracy of a measurement of the light absorption by a sample, however, is limited by the characteristics of at least one of the sample, the instrument, and the operating environment of the instrument. For example, ultraviolet light of a wavelength shorter than about 250 nm is highly absorbed as it passes through air. Thus, for an instrument in an environment that is other than evacuated, the intensity of light impinging upon the light detector configured for a wavelength shorter than about 250 nm is very low typically. Additionally, the intensity of all wavelengths of light are commonly measured using a single light detector or array with a time constant for integration of the received signal that is set based the response at a single wavelength, such that the maximum intensity of the incident light detected does not saturate the light detector.

Figure 1:
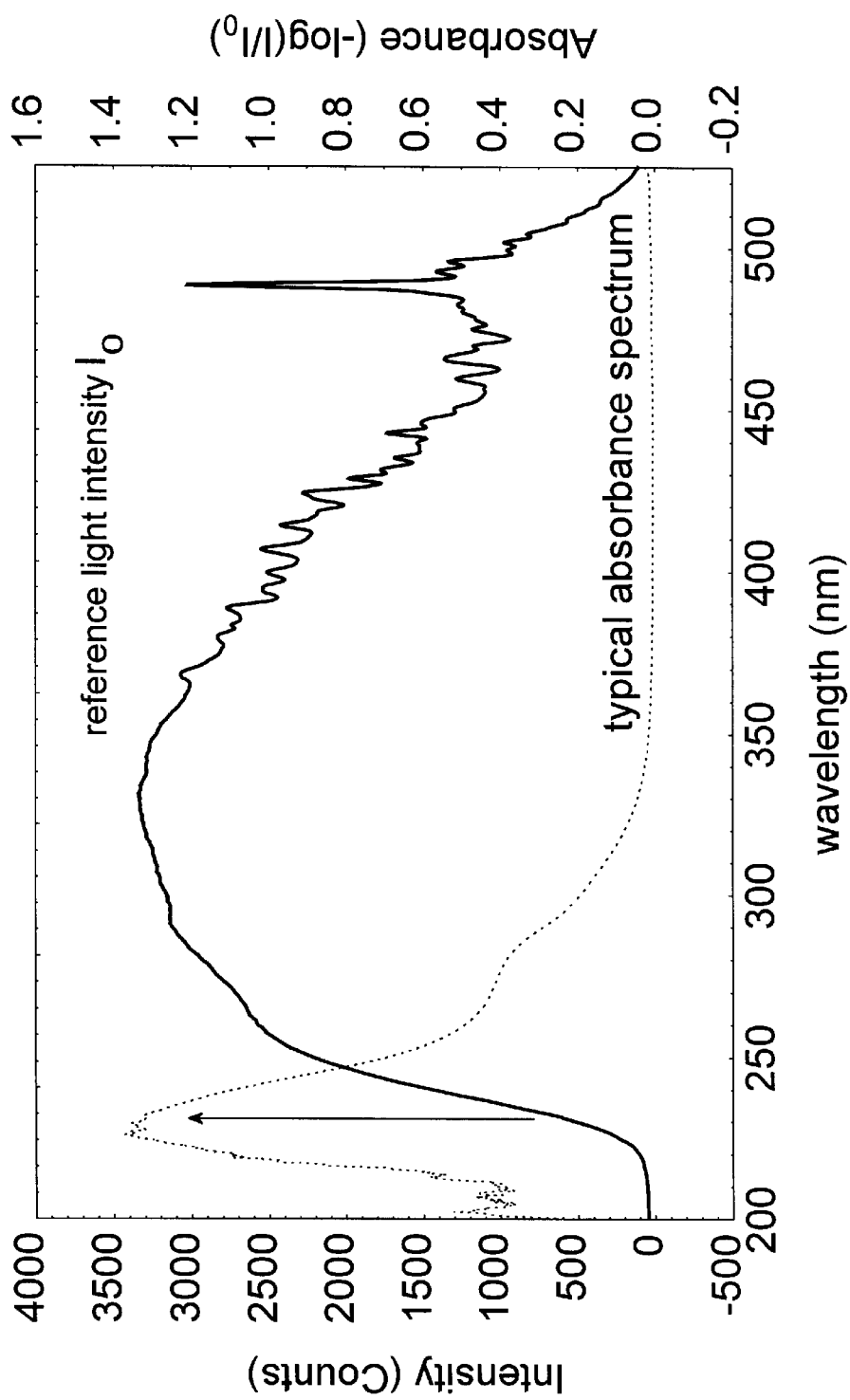
FIG. 1 shows a typical absorbance spectrum for a sample obtained using a prior art UV-visible spectrophotometer.

Referring to FIG. 1, a reference intensity spectrum obtained using a prior art UV-visible spectrophotometer is shown. The maximum intensity of the reference spectrum occurs at approximately 340 nm, where a value of approximately 3500 counts is observed using a CCD based array detector. However, the intensity of the reference spectrum at 230 nm is only approximately $I_o$=700 counts, or just 20% of the maximum intensity observed at 340 nm. It can be appreciated by those skilled in the art that the accuracy of a light absorbance measurement increases with increasing illumination intensity until the limit where the photodetector response becomes saturated or non-linear with respect to intensity. The digital resolution and dynamic range of a spectrometer are fixed by the design of the system optics and detector electronics. The electronics, including the analog to digital conversion are typically independent of wavelength. Consequently, for a case as illustrated in FIG. 1, the digital resolution and maximum dynamic range at 230 nm is less than 20% of the digital resolution and maximum dynamic range that would exist if the light detector was optimized to the lower incident light intensity at 230 nm. The measured signal is further lowered, as shown in FIG. 1, by the intense light absorption by a sample at 230 nm, which corresponds to the peak absorbing active spectral region of the sample.

Figure 2:
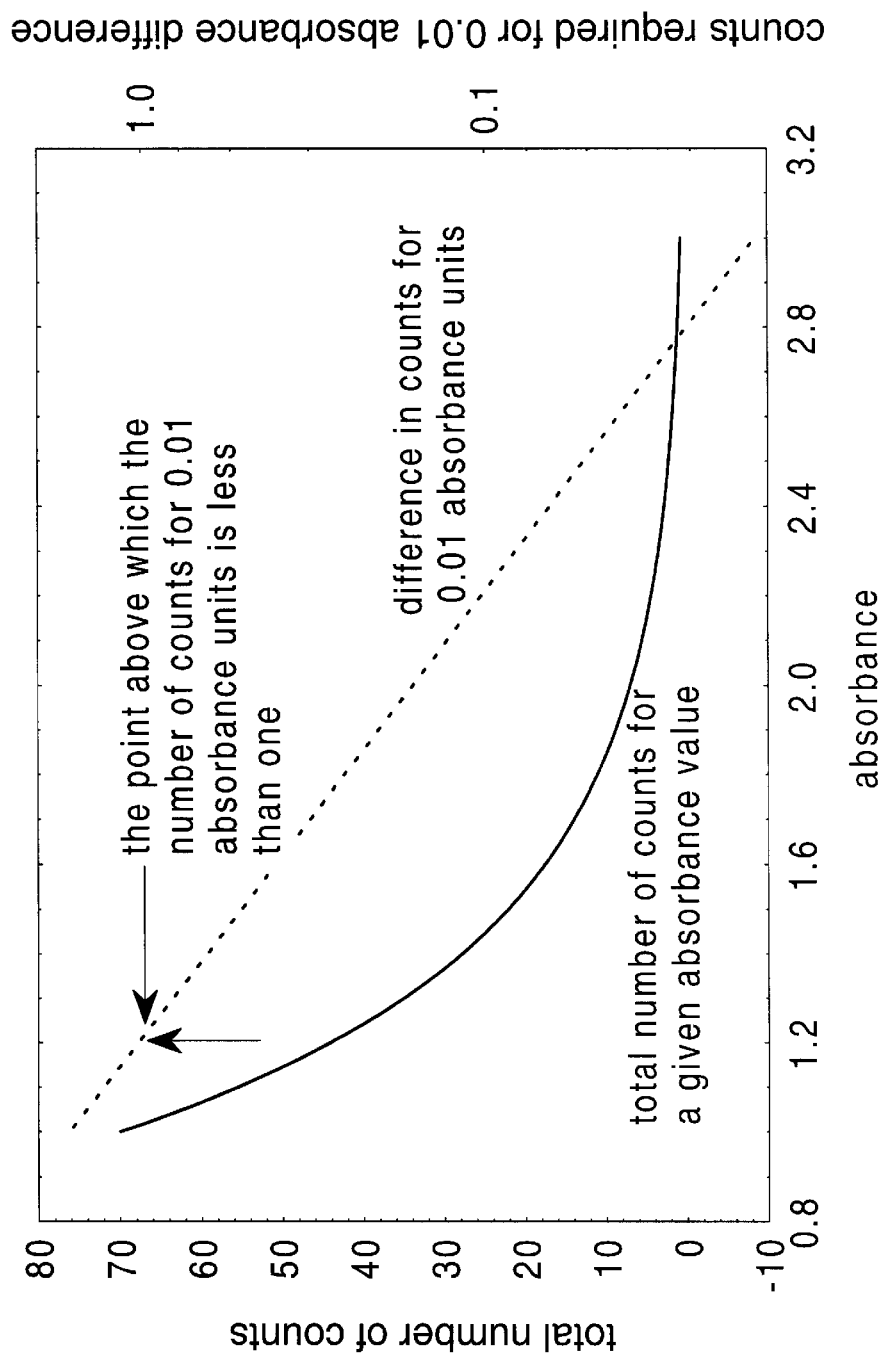
FIG. 2 is a plot showing a relationship between the number of counts required for a 0.01 absorbance difference and the measured absorbance of light by a sample, assuming a an intensity of light incident upon the sample of $I_o$=700 counts.

Referring to FIG. 2, a plot illustrating the total number of counts corresponding to a given absorbance value versus a given absorbance value is shown. It will be appreciated after an examination of FIG. 2 that more complete light absorption by the sample results in fewer counts by the light detector. Further, as shown in FIG. 2, the number of counts required for a 0.01 absorbance unit difference decreases logarithmically with increasing absorbance (note log scale for axis). With specific reference to the absorbance spectrum shown in FIG. 1, the absorbance at 230 nm is approximately 1.3 absorbance units, where according to Equation (1) the relationship between absorbance and light intensity is $A=-\log(I/I_o)$. For 1.3 absorbance and $I_o$=700 counts, the intensity of light reaching the light detector is about 35 counts and the difference between 1.30 absorbance and 1.31 absorbance measurements is less than one count. Insufficient digital resolution at high absorbance values leads to less accurate measurements that are other than suitable for detecting small differences in the amount of light absorbed by a sample. Ideally, the measurement of light absorbance by the sample at each different predetermined wavelength is made using the maximum light intensity that the light detector can measure at each particular wavelength.

Figure 3:
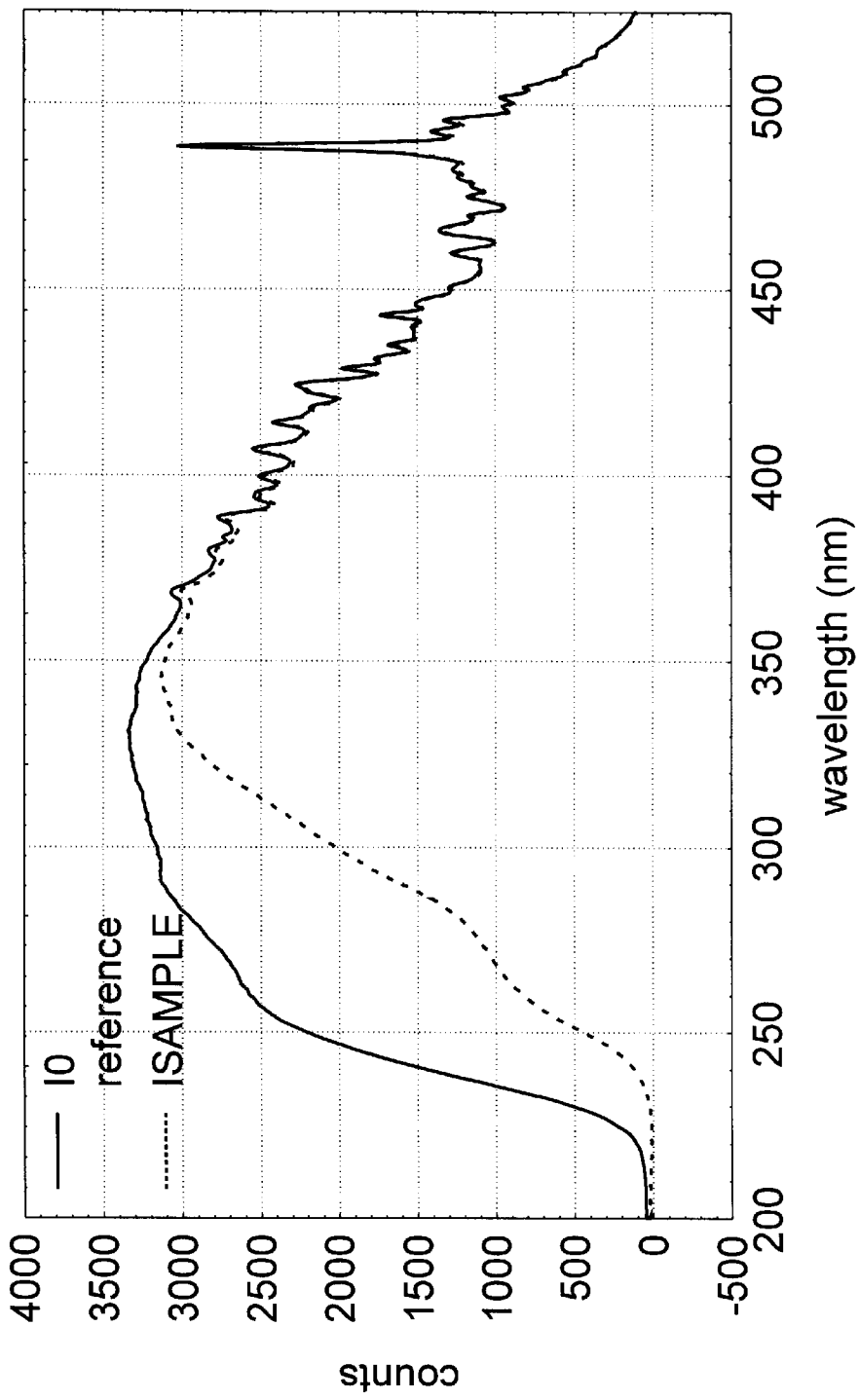
FIG. 3 shows a transmittance spectrum of a same sample that produced the absorption spectrum shown in FIG. 1, obtained using a prior art UV-visible spectrophotometer.

Referring to FIG. 3 the problem of insufficient digital resolution at low absorbance is illustrated. The reference spectrum of FIG. 1 is reproduced in FIG. 3 to facilitate comparison with a measured transmittance spectrum of the sample. A transmittance spectrum is a plot of I versus wavelength whereas an absorbance spectrum is a plot of $-\log(I/I_o)$ versus wavelength. At any wavelength where $I/I_o$=1 there is zero absorbance, also known as 100% transmittance, of the incident light. Unfortunately, when the transmittance spectrum of the sample is substantially coincident with the reference spectrum, it is often difficult to extract useful information pertaining to the characteristics of interest of the sample. Further, light absorption measurements performed at very low absorbance values are to be viewed with some uncertainty because such measurements are statistically prone to errors because difference between the reference signal and sample signal are low. In such a case, it is desired to increase the absorption of light by the sample, which according to Equation (1) is accomplished by increasing the path length of the light passing through the sample. In addition, cases where there is high absorbance can often lead to low sample signal, which hurts the statistical accuracy of the measurements. In this case, it is desired to decrease the absorption of light by the sample, which according to Equation (1) is accomplished by decreasing the path length of the light passing through the sample.

Figure 4:
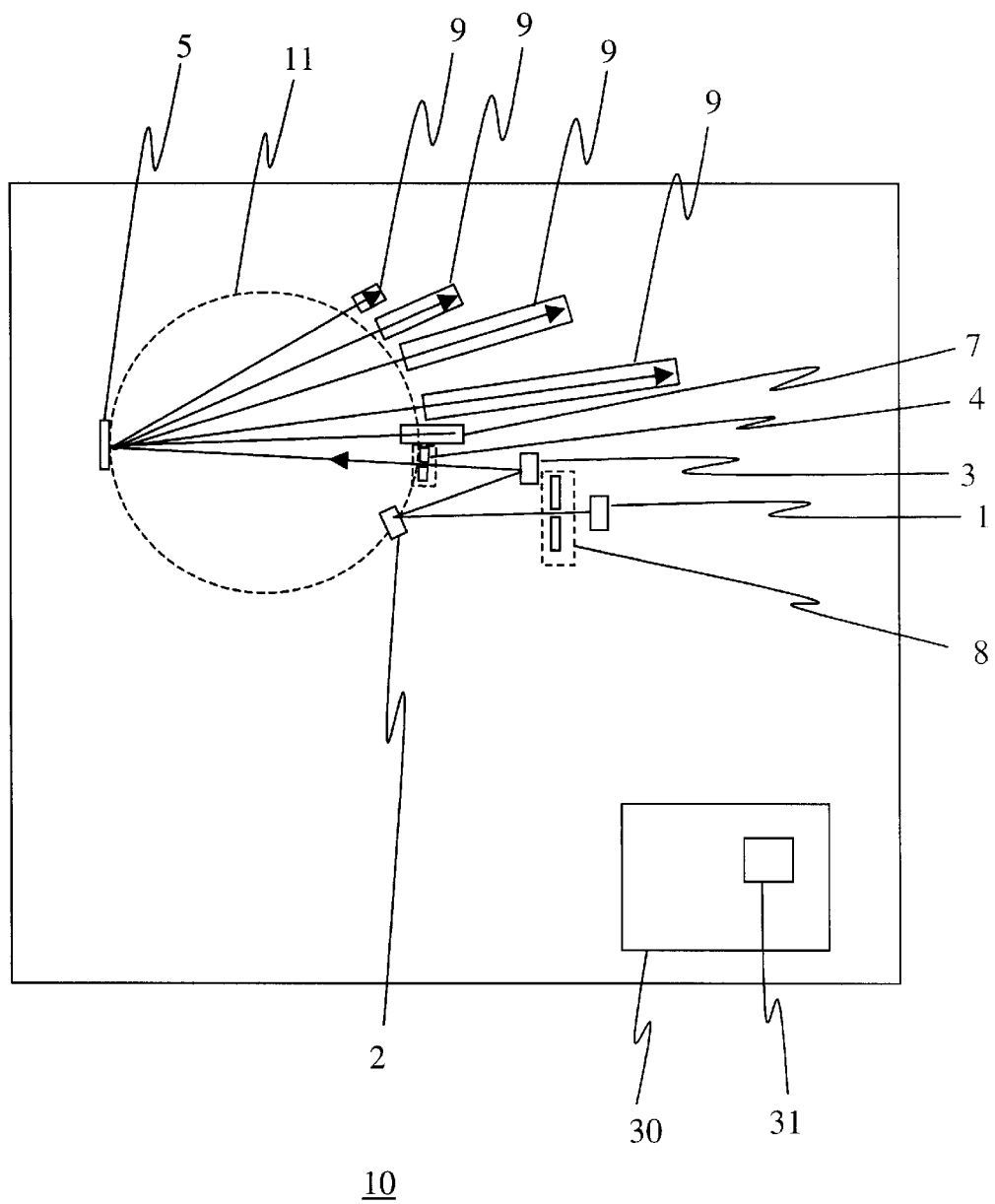
FIG. 4 is a simplified view of a preferred embodiment according to the present invention.

Referring to FIG. 4, a simplified view of an apparatus for the measurement of light absorption by a fluid sample according to the present invention is shown generally at 10. The apparatus is a variable path-length spectrophotometer that measures the optical transmission through a substantially the same fluid sample at eight (8) different predetermined wavelengths between 230 and 450 nm. The complete design is developed from a classical Rowland circle spectrometer and was developed to fit within a fairly compact system. The apparatus includes: a source 1; a stop 8; a concave mirror 2; a fold mirror 3; an entrance slit 4; a dispersive element in the form of a concave diffraction grating 5; a beam stop 7; and a plurality of channel detectors 9. In FIG. 4 the plurality of channel detectors includes four (4) separate channel detectors, detecting at wavelengths of 250 nm, 300 nm, 400 nm, and 450 nm, respectively. However, it is anticipated that a number of channel detectors other than four may be used, in dependence upon a specific requirement of a user of the apparatus 10. The source 1, in the form of a xenon arc lamp, launches polychromatic light of a desired range of wavelengths along an initial optical path, wherein the stop 8, the concave mirror 2, the fold mirror 3, the entrance slit 4, and the concave diffraction grating 5 are all disposed within said initial optical path. The stop 8 limits the cone size of the polychromatic light propagating along the initial optical path, which would otherwise contribute stray light errors and would lower the accuracy of the light absorption measurement. The concave mirror 2 is for reimaging the polychromatic light so that it impinges upon the entrance slit 4 with minimum horizontal spread. The fold mirror 3 reduces packaging size of the instrument Advantageously, because the system is folded, astigmatism is inherent, which allows a simple instrument design to be implemented using minimal optical elements for focusing and directing the light, as will be discussed in greater detail below. The entrance slit 4, the dispersive element 5 and a target slit 6 (see FIGS. 5 and 6) of each channel detector 9 of the plurality of channel detectors are disposed along the circular path of a Rowland circle 11.

Additionally, the apparatus shown generally at 10 includes a processor 30, for example a personal computer, in communication with the variable path-length spectrophotometer, as shown in FIG. 4. The processor 30 is for executing computer code for controlling the spectrophotometer, for storing in a memory 31 of the processor at least data received from the spectrophotometer, and for performing mathematical operations including converting the raw spectrophotometer data to absorbance values and calculating ratios of absorbance values.

The Rowland circle 11 diameter is a same as the radius of curvature of the grating. Spectrogon produces concave gratings and their smallest radius of curvature available is 400 mm. Therefore, the diameter of the Rowland circle was set at 400 mm or 16" to minimize system size. In order to have adequate angular separation between the various detector channels, the grating has 1200 lines/mm and is 50 mm in diameter. The intrinsic resolution of the spectrometer is finer than 0.01 nm. Because of this, the entrance slit of the spectrometer and the slits for each of the detector channels are typically opened up approximately 0.5 to 1 mm respectively, making the system very efficient.

The concave diffraction grating 5 is for dispersing the polychromatic light propagating along the initial optical path in dependence upon wavelength, to direct light at each of a plurality of different predetermined wavelengths along one of a plurality of different secondary optical paths. The concave diffraction grating 5 has a concave surface onto which is etched a plurality of very closely spaced features in the form of lines or grooves. The lines are disposed approximately parallel to one another, each line exposing a reflective surface. The spacing between the lines is on the order of the wavelength of the light that is being diffracted, resulting in both constructive and destructive interference of the multiply reflected light. Bright spots result where reflected light of a same wavelength interferes constructively and is focused. It is a feature of a concave diffraction grating that the diffracted light of different wavelengths is focused at different points in space that lie approximately along a circular path known as a Rowland circle 11 if the entrance slit 4 is also located on the same circle. The diameter of the Rowland circle is equal to the radius of curvature of the concave diffraction grating 5. In order to achieve the greatest separation between each of a plurality of predetermined wavelengths, a concave diffraction grating 5 having approximately 1200 lines per mm should be used. Of course, concave diffraction gratings with other than 1200 lines per millimeter could be used, resulting in a different inherent resolution for the instrument and a different spacing along the Rowland circle 11 of the light for each predetermined wavelength.

The concave diffraction grating 5 is the only optical element that is common to every secondary optical path. Advantageously, the concave diffraction grating 5 provides light of a first predetermined wavelength propagating along a first secondary optical path and at least light of a second other predetermined wavelength propagating along at least a second other secondary optical path. Each different secondary optical path, other than the zero-order secondary optical path, passes through a separate channel detector, said channel detector disposed within a unique secondary optical path and located in space at a point along the circular path of a Rowland circle in dependence upon the predetermined wavelength of light to be detected. A beam stop 7 is disposed along the zero order secondary optical path for intercepting zero order light diffracted from the diffraction grating, which would otherwise be a source of stray light and would introduce noise, thus decreasing the accuracy of the measurement. Additionally, the entrance slit 4 is disposed along the Rowland circle at the diffraction angle −3°, thus allowing the beam stop 7 to be disposed along the Rowland circle at the diffraction angle 3°. Offsetting the entrance slit slightly from 0° obviates the problem of having zero order light reflected directly back at the source 1 by the concave diffraction grating 5.

Figure 5:
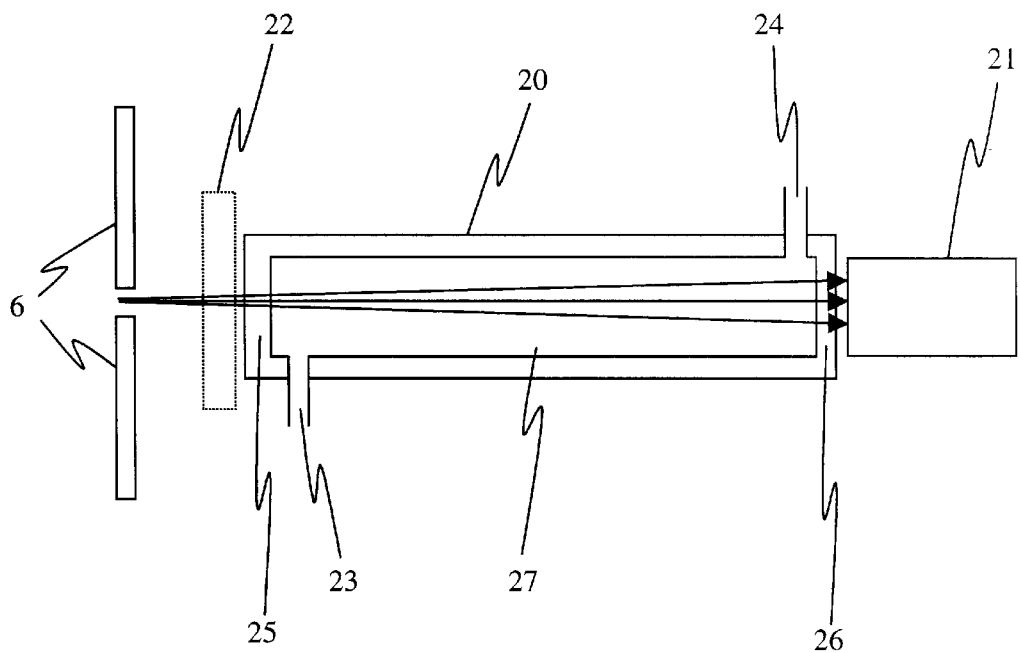
FIG. 5 is a simplified block diagram of a detector channel geometry of the present invention for the 250 nm, 300 nm, 350 nm, 400 nm and 450 nm channels.

Referring to FIG. 5, a simplified block diagram illustrating the configuration of the 250 nm, 300 nm, 350 nm, 400 nm and 450 nm channel detectors is shown. Each channel detector comprises: a target slit 6; a sample cell 20 having at least a first light transmissive end face 25 and a second other light transmissive end face 26 for the transmission of light through the sample cell; and a light detector 21. The sample cell has a containing portion 27 for containing a fluid sample, wherein the optical path length of the light through the fluid sample is a same as the length of the containing portion 27. An inlet port 23 in communication with the containing portion 27 is provided for the admitting a fluid sample into the containing portion 27 of the sample cell 20. An outlet port 24, also in communication with the containing portion of the sample cell 20, is additionally provided for allowing the fluid sample to exit the containing portion 27 of the sample cell 20. In a preferred embodiment of the invention the length of the containing portion 27, and consequently the optical path length through the fluid sample, is different for every channel detector. Further, the optical path length is optimized in dependence upon the predetermined wavelength of light and the fluid sample such that a detected value is approximately central to a linearly varying range of values supported by the detector. Preferably, the inlet port 23 is disposed proximate to the first light transmissive end face 25 of the sample cell 20 and the outlet port 24 is disposed proximate to the second other light transmissive end face 26 of the sample cell 20. The direction of fluid flow into the sample cell 20 does not impact performance, such that optionally the outlet port 24 is disposed proximate to the first light transmissive end face 25 of the sample cell 20 and the inlet port 23 is disposed proximate to the second other light transmissive end face 26 of the sample cell 20.

An optional band-pass filter 22 is further required for the 400 nm and 450 nm channels that also receive second-order diffracted light at 200 nm and 225 nm. Optional band-pass filters on the other channels will reduce stray light and will further increase the accuracy of each measurement. Advantageously, additional focusing optics for each channel is not necessary due to the inherent astigmatism of the instrument. Light is focused onto the target slit 6 by the concave diffraction grating 5, forming a sharp vertical line image that matches the width of the target slit 6. The light diverges horizontally after it passes through the target slit 6 such that a sharp horizontal line image is produced at a plane near the Sagital focus some distance r beyond the target slit 6. When an optical element such as a light transmissive endface of a first sample cell is placed in vicinity to the Sagital focus, the target slit performs a function of focusing light at a predetermined wavelength onto the optical element. The light detector 21 is positioned intermediate to both of the Tangential focus point and the Sagital focus point. There is, however, no compelling reason to place the light detector at a point that is precisely, or even substantially near to the Medial or the point of mid focus if the size of the light detector 21 is large enough to collect all the signal seen at either the Tangential or Sagital focus. In the system described with reference to FIG. 4, the beam of light is confined within a spot size of less than 10 mm diameter between both the Tangential and Sagital foci, and hence a 10-mm diameter light detector 21 detects the full intensity of the transmitted light, even when the light detector is disposed substantially nearer to one of the Tangential focus point or the Sagital focus point. Because the beam size hits a minimum at the Medial focus, a light detector 21 that is smaller than the size of the target slit 6 should be placed near to the Medial focus. Advantageously, the inner diameter of the containing portion of the sample cell 20 is such that no light interacts with the inner wall of the sample cell 20. Further advantageously, refraction inside the fluid-containing sample cell decreases the divergence of the light beam and moves the Sagital focus back, allowing longer sample cell lengths to be used without additional optics.

Figure 6:
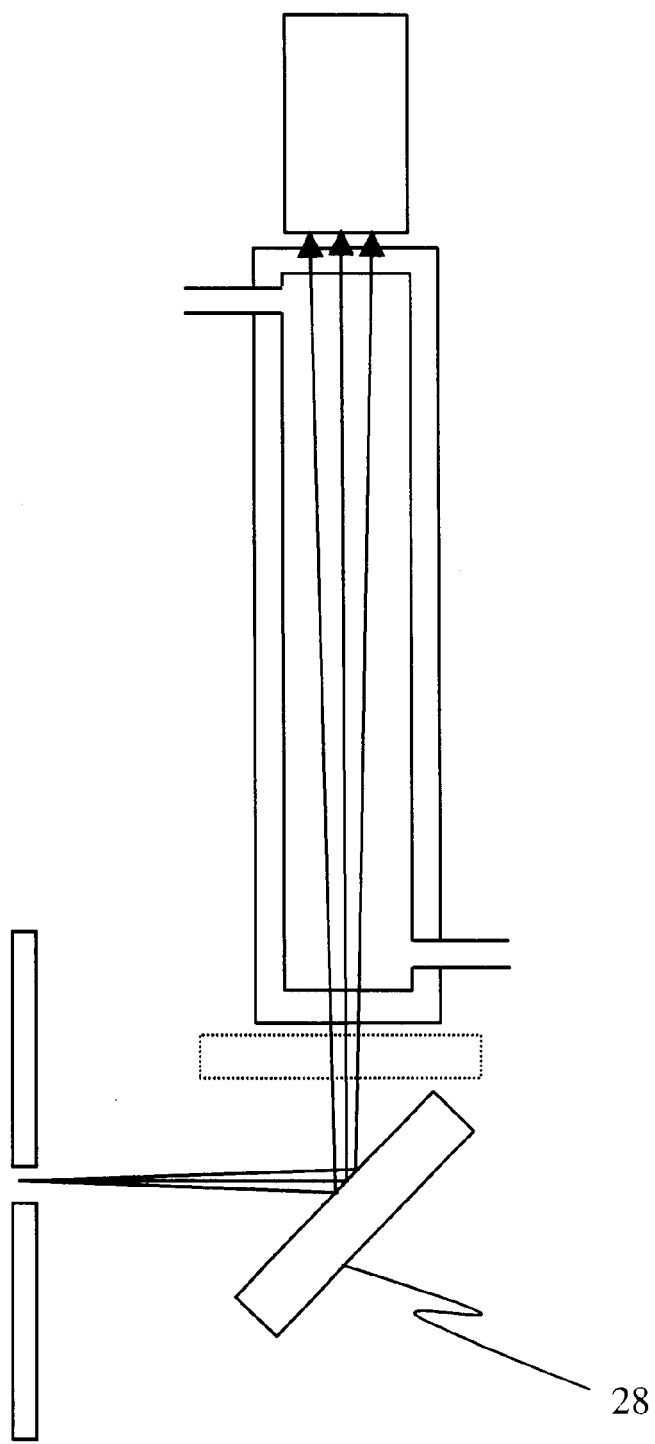
FIG. 6 is a simplified block diagram showing the detector channel geometry of the present invention for the 230 nm, 280 nm and 320 nm channels.

Referring to FIG. 6, a simplified block diagram illustrating the configuration of the 230 nm, 280 nm and 320 nm channel detectors is shown. In FIG. 6, parts common to the aforementioned apparatus are designated by like numerals and omitted in their description. The only additional optical element required in the 230 nm, 280 nm and 320 nm channel detectors is a fold mirror 28, positioned 20 mm behind the target slit, for directing the light propagating along the 230 nm, 280 nm and 320 nm channels through an angle substantially 90 degrees from the direction of propagation of light. The fold mirror 28 is required to resolve packaging issues that arise because there is insufficient physical space in only one plane to accommodate the 230 nm, 250 nm, 280 nm, 300 nm and 320 nm channels, which are closely spaced along the arc of a Rowland circle 11 with a radius of curvature as small as the one being proposed herein. The circumferential distance between the target slits of the 230 nm and of the 320 nm channels is approximately 10 mm. Obviously, fitting five separate channels in the same horizontal plane cannot be done, as the mechanical walls and holders for the light detectors require more space.

Thus the individual channels are spatially separated from each other along the arc of the Rowland circle, and additionally the 230 nm, 280 nm and 320 nm channels are arranged approximately perpendicular to the 250 nm, 300 nm, 350 nm, 400 nm and 450 nm channels, providing separation in a second dimension. Such an arrangement of the channel detectors facilitates the packaging of the instrument into a very small unit size, satisfying design criteria for portability. The fold mirrors add only an additional 40 mm to the total distance traveled by the light between the target slits and the first light transmissive end face of the sample cell. Advantageously, each of the channels for measuring the absorption by the sample of light in the wavelength range of 230 nm to 320 nm requires a total optical path length that is approximately 40 mm longer than the shortest attainable optical path length. The additional 40 mm of total path length ensures that the light detector for each channel is located substantially close to the point of mid focus, such that the light beam is confined to an area equal to or smaller than the operative surface of the light detector. In a preferred embodiment of the invention the length of the containing portion 27, and consequently the optical path length through the fluid sample, is different for every channel detector. Further, the optical path length is optimized in dependence upon the predetermined wavelength of light and the fluid sample such that a detected value is approximately central to a linearly varying range of values supported by the detector.

The apparatus shown generally at 10 differs from the prior art dispersive systems in that the dispersive element 5 is disposed between the at least a light source 1 and each sample cell 20 of the plurality of sample cells. The fluid sample contained within the containing portion 27 of each sample cell 20 of the plurality of sample cells is irradiated with substantially monochromatic light. Further, the dispersive element 5 of the apparatus shown generally at 10 does not scan through a continuum of wavelengths, instead the wavelength of substantially monochromatic light that are used to irradiate the fluid sample contained within each sample cell is pre-selected in dependence upon the position of each sample cell relative to the diffraction grating normal. A separate detector is associated with each sample cell 20 of the plurality of sample cells and optimized to detect light at the pre-selected wavelength propagating through that sample cell. Typically in prior art dispersive systems, a dispersive element is disposed between a single sample cell and a single detector, such that the sample is irradiated with polychromatic radiation and the polychromatic transmitted light is subsequently dispersed in dependence upon wavelength, prior to detection at the detector. Of course, the detector detects light optimally at one wavelength only, such that the error associated with light absorption measurements at wavelengths of light other than the optimized wavelength are large relative to an error obtained under conditions optimized for the measured wavelength.

Figure 7:
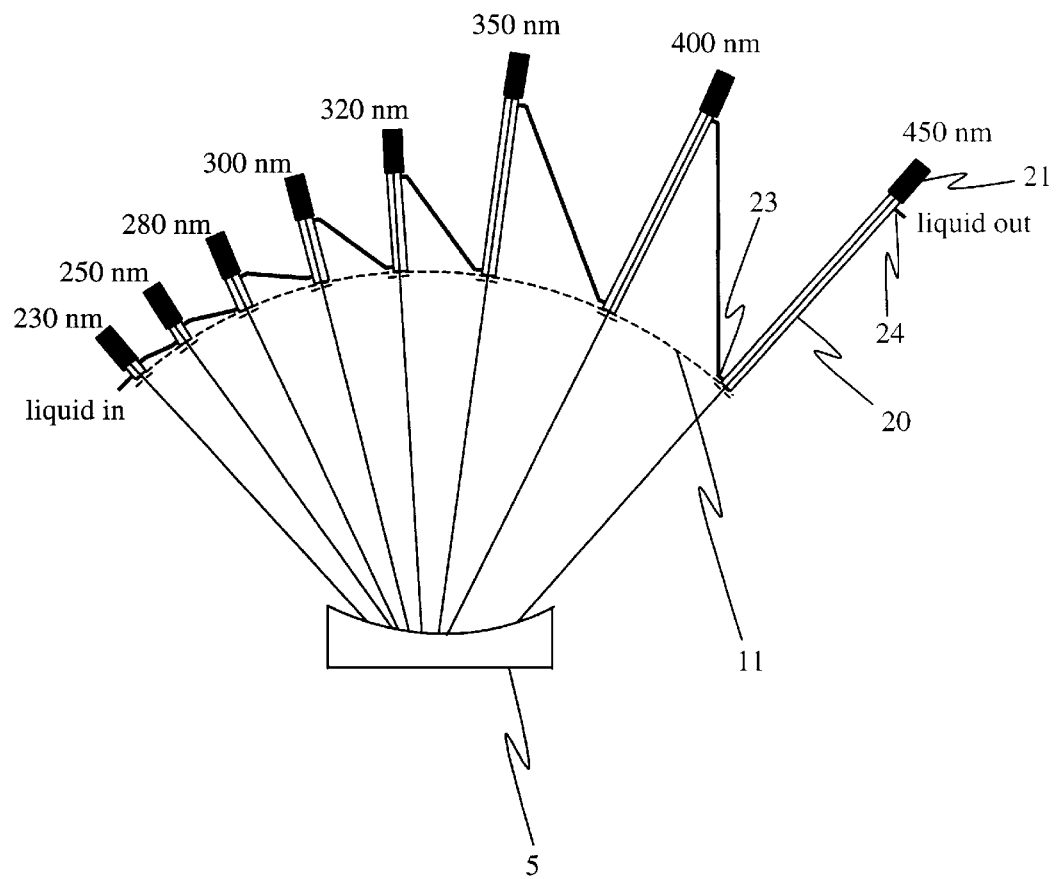
FIG. 7 is a simplified block diagram showing the arrangement of the detector channels to allow for variable wavelength-dependent fluid sample path lengths.

Referring to FIG. 7, a preferred embodiment of the invention is shown in which the sample cells are connected sequentially such that the outlet port of a first sample cell communicates with the inlet port of a second sample cell, the outlet port of a second sample cell communicates with the inlet port of a third sample cell, etc. Such an arrangement allows a continuous stream of a fluid sample to flow through all sample cells sequentially, and thus each sample cell contains substantially the same sample. Further advantageously, the arrangement allows a process stream to be sampled continuously and automatically simply by diverting a small portion of the process stream through the inlet port 23 of a first sample cell and taking the sample off again through the outlet port 24 of a final sample cell. Of course, the fluid sample could also be made to flow in the reverse direction by diverting a small portion of the process stream through the outlet port 24 of the final sample cell and taking the sample off again through the inlet port 23 of the first sample cell. It is to be understood that the fold mirror 28 disposed within each of the 230 nm, 280 nm and 320 nm channel detectors are omitted for clarity and does not imply that the plurality of channel detectors is contained within a single plane.

Figure 8:
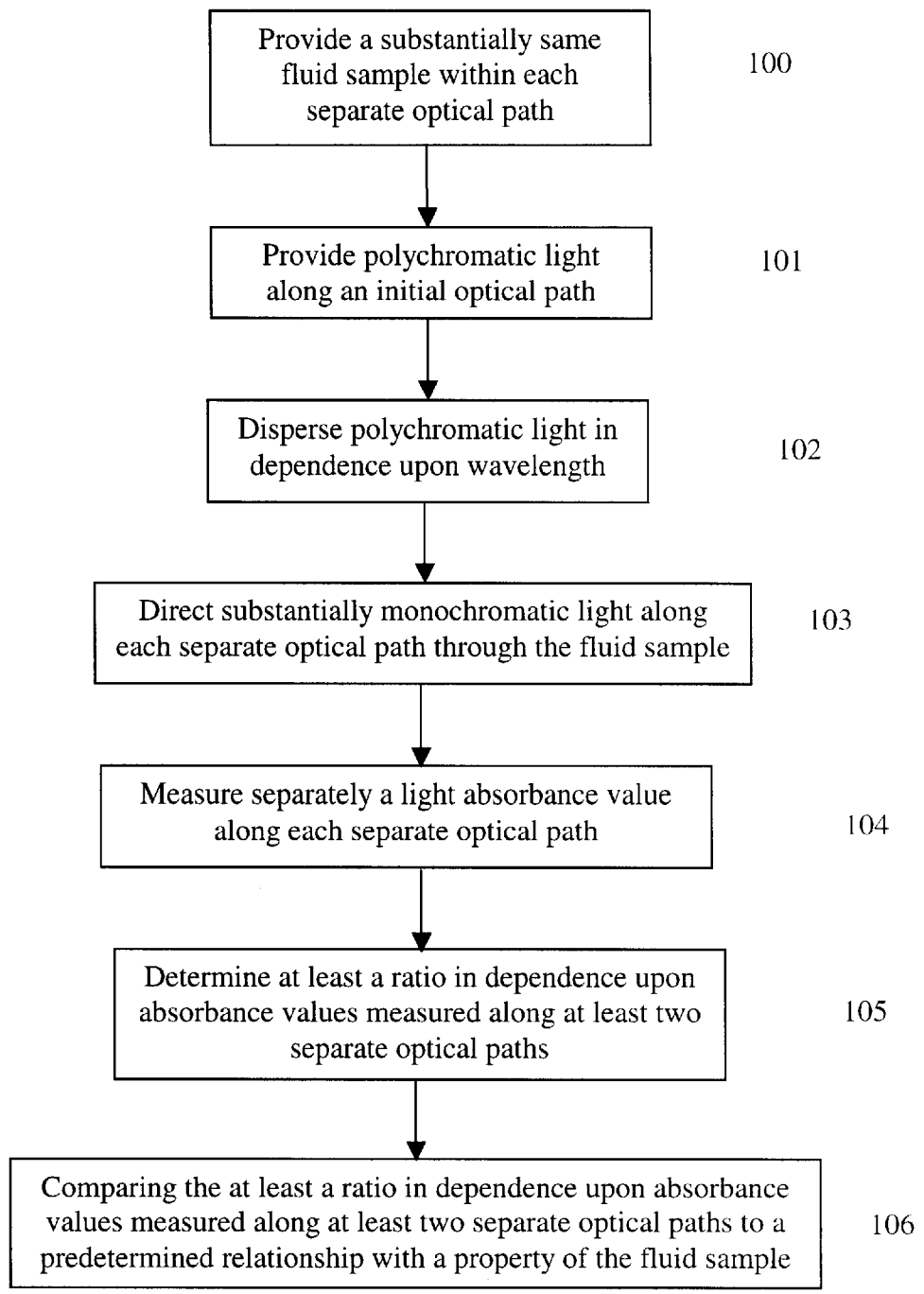
FIG. 8 is a simplified flow diagram of a method for characterizing a fluid sample using absorbance ratios measured at two or more wavelengths.

Referring to FIG. 8, shown is a simplified flow diagram of a method for measuring at least an absorbance of light by a fluid sample according to the present invention. At step 100 a fluid sample is provided, such that a same fluid sample is contained within each containing portion of each sample cell of the plurality of sample cells. Preferably, a fluid sample is diverted from an effluent or other process stream and directed through a first inlet port that is in communication with a first containing portion of a first sample cell. The fluid sample is directed to flow through the first sample cell and exit via a first outlet port of the first sample cell. Most preferably, the first outlet port of the first sample cell is in communication with both the first containing portion of the first sample cell, and a second inlet port of a second next sample cell, such that the fluid sample flows through the containing portion of each separate sample cell in sequence. Advantageously, the fluid sample contained within each containing portion of each sample cell is a substantially same fluid sample.

At step 101 polychromatic light is provided along an initial optical path and is angularly dispersed in dependence upon wavelength at step 102. Light at each of a plurality of predetermined wavelengths is directed along a plurality of separate optical paths through individual fluid samples contained within the containing portion of each separate sample cell, step 103. The path length through each sample cell is optimized in dependence upon the fluid sample and the predetermined wavelength of light propagating through the sample cell. Specifically, the path length is selected such that the amount of light absorbed by the fluid sample tends toward an amount of light absorption approximately central to an approximately linearly varying region of an absorption curve for the fluid sample at each predetermined wavelength. At step 104 an absorbance value is determined separately for the absorption of light at each predetermined wavelength by the same fluid sample. As will be obvious to one of skill in the art, a prior measurement of light transmittance along each separate optical path when a reference sample is present is performed prior to determining an absorbance value for the fluid sample of interest.

Alternatively, baseline data stored in a memory of the apparatus is used to determine the absorbance values at step 104.

Steps 105 and 106 are optionally performed in the current method. For example, a microprocessor unit 30 for performing mathematical operations calculates at least a ratio of two absorbance values at step 105 in dependence upon a predetermined preference. At step 106 the at least a ratio is compared to a predetermined relationship between the at least a ratio and one of a physical property and a concentration value of the fluid sample. For instance, a memory 31 of the microprocessor 30 includes previously measured data relating the at least a ratio to one of a physical property or concentration value of the fluid sample.

In the embodiment of the invention described herein, the light source is a xenon arc lamp. Advantageously, a xenon arc lamp provides a high output of radiation at the shorter wavelengths of the ultraviolet region. Further advantageously, the xenon arc lamp provides peaks at 230 nm and 250 nm that are suitable for calibrating wavelength measurements of the apparatus. Alternatively, at least one of a high-powered deuterium lamp and a tungsten filament lamp are used as the light source. Further alternatively, a plurality of lasers or a plurality of tunable lasers could be used for providing monochromatic light at a plurality of different wavelengths.

In the embodiment of the invention described herein, the light-dispersing element is a reflective concave diffraction grating, however, it is anticipated that other types of light-dispersing elements, such as for example a transmissive diffraction grating, could be used without departing significantly from the teachings of the present invention. Alternatively, the light dispersing element is replaced with another light separating element such as: a tunable Farbry-Perot interference filter as disclosed in U.S. Pat. No. 4,779,959, issued to Saunders; a, variable filter as described in U.S. Pat. No. 5,144,498, issued to Okamoto, et al. and U.S. Pat. No. 5,218,473, issued to Seddon, et al; a multi-line narrowband-pass filter as described in U.S. Pat. No. 5,410,431, issued to Southwell; and, a series of wavelength selective dichroic coatings, as described in U.S. Pat. No. 6,072,633, issued to Park, et al.

Further optionally, the method according to the instant invention is performed with respect to a reference fluid sample. Steps 101 to 104 and optionally 105 and 106 are first performed for a fluid sample, and are then repeatedly performed for a reference fluid sample. A microprocessor 30 is then used to calculate a first absorbance value relating to the absorbance of light at the first wavelength by the fluid sample, in dependence upon the detected first value of an intensity of light of the fluid sample and the detected first value of an intensity of light of the reference fluid sample; and, a second absorbance value relating to the absorbance of light at the second other wavelength by the fluid sample, in dependence upon the detected first value of an intensity of light of the fluid sample and the detected first value of an intensity of light of the reference fluid sample.

It is an advantage of the preferred embodiment of the present invention that the diffracted light of different wavelengths is focused along a circular path known as a Rowland circle, which facilitates the use of independent light detectors for each different secondary optical path, said light detectors optimized for the light intensity of each predetermined wavelength of light. The absorption of wavelengths of light other than the predetermined wavelengths of light described herein could be performed by providing a means for the operator of the instrument to drive the position of at least a channel detector to a different position along the Rowland circle. Of course the length of the sample cell is optimized for only one specific wavelength of light and hence lower accuracy is expected for measurements performed at other wavelengths, Alternatively, the manufacturer could preset the positions of the channel detectors along the Rowland circle according to the needs or anticipated needs of the purchaser and additionally provide sample cells that are of an appropriate length.

In the embodiment of the invention described herein, a plurality of separate sample cells, each separate sample cell for containing a fluid sample within a containing portion thereof, is described. Each separate sample cell is disposed within a separate optical path, such that substantially monochromatic light at one wavelength of the plurality of predetermined wavelengths of light propagates through the containing portion of each sample cell in dependence upon the position of the sample cell along the Rowland circle. Alternatively, a same sample cell is disposed within at least two different optical paths, the same sample cell for containing a same fluid sample within a same containing portion thereof. The same sample cell is shaped for providing a first optical path length through the same fluid sample along the first optical path, a second different optical path length through the same fluid sample along the second different optical path, and an $n^{th}$ different optical path length through the same fluid sample along the $n^{th}$ different optical path, wherein n is the number of predetermined wavelengths.

The inherent astigmatism of the instrument, which is introduced by the fold-mirror within the initial optical path, obviates the need to use additional optical elements to confine the light beam within the containing portion of the sample cell, which simplifies instrument design and reduces the problems associated with misalignment of the optical elements. Further advantageously the radius of the Rowland circle is equal to the radius of curvature of the concave grating, which allows a compact instrument design to be implemented using a commercially available concave grating with a small radius of curvature.

Numerous other embodiments may be envisaged without departing from the spirit or scope of the invention.

What is claimed is:

1. A method of measuring light absorption by a fluid sample comprising the steps of:
   a) providing polychromatic light along an initial optical path;
   b) dispersing the polychromatic light in dependence upon wavelength:
      to direct light at a first predetermined wavelength along a first optical path having a first path length through the fluid sample; and,
      to direct light at a second other predetermined wavelength along a second other optical path having a second other path length through the fluid sample;
   c) detecting an intensity of light at the first predetermined wavelength after it has propagated the first optical path length through the fluid sample using a first light detector disposed within the first optical path and supporting a first range of detected values; and,
   d) detecting an intensity of light at the second other predetermined wavelength after it has propagated the second optical path length through the fluid sample using a second other light detector disposed within the second other optical path and supporting a second range of detected values, wherein the first path length is selected in dependence upon the first wavelength and the fluid sample such that a detected first value is within a portion of the first range wherein substantial variations in optical intensity result in substantial changes in the first value, and,
   wherein the second path length is selected in dependence upon the second other wavelength and the fluid sample such that a detected second value is within a portion of the second range wherein substantial variations in optical intensity result in substantial changes in the second value, and,
   wherein the first light detector is angularly disposed along an arc section of a Rowland circle in dependence upon the first wavelength of light and the second other light detector is angularly disposed along a same arc section of a same Rowland circle in dependence upon the second other wavelength of light.

2. The method claimed in claim 1, wherein the first path length is selected in dependence upon the first wavelength and the fluid sample such that the detected first value is substantially outside an approximately over saturated portion of the first range, and, wherein the second path length is selected in dependence upon the second other wavelength and the fluid sample such that the detected second value is substantially outside an approximately over saturated portion of the second other range.

3. The method claimed in claim 2, wherein:
   the fluid sample to be interrogated at the first wavelength is contained within a first containing portion of a first sample cell disposed within the first optical path and
   the fluid sample to be interrogated at the second other wavelength is contained within a second other containing portion of a second other sample cell disposed within the second optical path, and
   wherein the first containing portion and the second other containing portion are in fluid communication such that the first containing portion and the second other containing portion contain substantially a same fluid sample.

4. The method claimed in claim 3, comprising the additional steps of:
   e) repeating steps a) to d) with a reference fluid sample; and,
   f) calculating:
      a first absorbance value relating to the absorbance of light at the first wavelength by the fluid sample, in dependence upon the detected first value and the results of step e); and,
      a second absorbance value relating to the absorbance of light at the second other wavelength by the fluid sample, in dependence upon the detected second value and the results of step e).

5. The method claimed in claim 4, comprising the additional step of:
   g) determining a value for one of concentration and physical property of the fluid sample from a ratio between the first and second absorbance values determined in step f).

6. The method claimed in claim 4, wherein the amount of light absorbed by the fluid sample tends toward an amount of light absorption approximately central to an approximately linearly varying region of an absorption curve for the fluid sample at the first and at the second other wavelengths of light.

7. The method claimed in claim 6, wherein each predetermined wavelength of light of the plurality of different predetermined wavelengths of light is selected from the ultraviolet-visible region of the electromagnetic spectrum.

8. The method claimed in claim 7, wherein the predetermined wavelengths of light are approximately 230 nm, 250 nm, 280 nm, 300 nm, 320 nm, 350 nm, 400 nm and 450 nm.

9. A method of measuring light absorption by a fluid sample including a light absorbing species comprising the steps of:
   a) providing polychromatic light along an initial optical path;
   b) dispersing the polychromatic light in dependence upon wavelength:
      to direct light at a first predetermined wavelength along a first optical path having a first path length through the fluid sample; and,
      to direct light at a second other predetermined wavelength along a second other optical path having a second other path length through the fluid sample;
   c) detecting an intensity of light at the first predetermined wavelength after it has propagated the first optical path length through the fluid sample using a first light detector disposed within the first optical path and supporting a first range of detected values; and,
   d) detecting an intensity of light at the second other predetermined wavelength after it has propagated the second optical path length through the fluid sample using a second other light detector disposed within the second other optical path and supporting a second other range of detected values,
   wherein the first path length is selected in dependence upon the first wavelength and the fluid sample such that a detected first value is within a portion of the first range wherein substantial variations in optical intensity result in substantial changes in the first value, and,
   wherein the second path length is selected in dependence upon the second other wavelength and the fluid sample such that a detected second value is within a portion of the second range wherein substantial variations in optical intensity result in substantial changes in the second value.

10. The method claimed in claim 9, wherein the first path length is selected in dependence upon the first wavelength and the light absorbing species such that the detected first value is substantially outside an approximately over saturated portion of the first range, and, wherein the second path length is selected in dependence upon the second other wavelength and the same light absorbing species such that the detected second value is substantially outside an approximately over saturated portion of the second other range.

11. The method claimed in claim 10, wherein
   the fluid sample to be interrogated at the first wavelength is contained within a first containing portion of a first sample cell disposed within the first optical path and
   the fluid sample to be interrogated at the second other wavelength is contained within a second other containing portion of a second other sample cell disposed within the second optical path, and
   wherein the first containing portion and the second other containing portion are in fluid communication such that the first containing portion and the second other containing portion contain substantially a same fluid sample.

12. The method claimed in claim 11, comprising the additional steps of:
   e) repeating steps a) to d) with a reference fluid sample; and,
   f) calculating:
      a first absorbance value relating to the absorbance of light at the first wavelength by the light absorbing species in dependence upon the detected first value and the results of step e); and,
      a second absorbance value relating to the absorbance of light at the second other wavelength by the same light absorbing species in dependence upon the detected second value and the results of step e).

13. The method claimed in claim 12, comprising the additional step of:
   g) determining a value for one of concentration and physical property of the fluid sample from a ratio between the first and second absorbance values determined in step f).

14. The method claimed in claim 12, wherein the amount light absorbed by the light absorbing species of the fluid sample tends toward an amount of light absorption approximately central to an approximately linearly varying region of an absorption curve for the sample at the first and at the second other wavelengths of light.

15. The method claimed in claim 14, wherein the first light detector is angularly disposed along an arc section of a Rowland circle in dependence upon the first wavelength of light and the second other light detector is angularly disposed along a same arc section of a same Rowland circle in dependence upon the second other wavelength of light.

16. The method claimed in claim 15, wherein each predetermined wavelength of light of the plurality of different predetermined wavelengths of light is selected from the ultraviolet-visible region of the electromagnetic spectrum.

17. The method claimed in claim 16, wherein the predetermined wavelengths of light are approximately 230 nm, 250 nm, 280 nm, 300 nm, 320 nm, 350 nm, 400 nm and 450 nm.

18. The method claimed in claim 17, wherein the measurement of light absorption by the light absorbing species of the fluid sample at the first predetermined wavelength of light and the measurement of light absorption by the light absorbing species of the fluid sample at the second other predetermined wavelength of light are performed during a substantially same overlapping period of time.

19. The method claimed in claim 9, wherein the step of dispersing the polychromatic light in dependence upon wavelength is performed using a light separating element selected from the group consisting of: a tunable Farbry-Perot interference filter; a linear variable filter; a multi-line narrowband-pass filter; and a plurality of wavelength selective reflective and transmissive dichroics.

20. An apparatus for measuring light absorption by a fluid sample comprising:
   at least a light source for providing polychromatic light along an initial optical path;
   a light separating element disposed within the initial optical path for receiving the polychromatic light from the at least a light source and for dispersing the polychromatic light in dependence upon wavelength to direct light at each of a plurality of different predetermined wavelengths along one of a plurality of different secondary optical paths, including a signal at a first predetermined wavelength of light propagating along a first secondary optical path and a signal at a second other predetermined wavelength of light propagating along a second other secondary optical path;

a first channel detector disposed within the first secondary optical path comprising:
   a) a first sample cell for containing a fluid sample within a containing portion thereof and having at least a light transmissive endface; and,
   b) a first light detector disposed for receiving light at the first predetermined wavelength from one of the at least a light transmissive endface of the first sample cell, light at the first predetermined wavelength propagating a first optical path length through the containing portion of the first sample cell;

a second channel detector disposed within the second other secondary optical path comprising:
   a) a second other sample cell for containing a fluid sample within a containing portion thereof and having at least a light transmissive endface; and,
   b) a second other light detector disposed for receiving light from one of the at least a light transmissive endface of the second other sample cell, light at the second other predetermined wavelength propagating a second different optical path length through the containing portion of the second other sample cell;

wherein the light separating element defines a Rowland circle, the first channel detector and the second other channel detector being angularly disposed along an arc section of the Rowland circle in dependence upon the first predetermined wavelength of light and the second other predetermined wavelength of light, respectively.

21. The apparatus claimed in claim 20, wherein the at least a light transmissive endface comprises a first light transmissive endface and a second light transmissive endface, and wherein each sample cell further comprises:
   an inlet port in communication with the containing portion of the sample cell for introducing the fluid sample into the containing portion of the sample cell and disposed substantially close to the first light transmissive endface; and
   an outlet port in communication with the containing portion of the sample cell for passing the fluid sample out of the containing portion of the sample cell and disposed substantially close to the second light transmissive end face.

22. The apparatus claimed in claim 21, wherein the outlet port of the first sample cell is in fluid communication with the inlet port of the second other sample cell, such that a fluid sample introduced into the first sample cell passes through the length of the first sample cell and of the second other sample cell in sequence via a single continuous fluid path.

23. The apparatus claimed in claims 20, further comprising:
   b) a first target slit disposed within the first secondary optical path for focusing light at the first predetermined wavelength provided by the light separating element onto one of the at least a light transmissive endface of the first sample cell; and,
   b) a second other target slit disposed within the second other secondary optical path for focusing light at the second other predetermined wavelength provided by the light separating element onto one of the at least a light transmissive endface of the second other sample cell.

24. The apparatus claimed in claim 23 wherein the light separating element is selected from the group consisting of: a tunable Farbry-Perot interference filter; a linear variable filter; a multi-line narrowband-pass filter; and a plurality of wavelength selective reflective and transmissive dichroics.

25. The apparatus claimed in claim 23 wherein the light separating element is a dispersive element selected from the group consisting of: a reflective diffraction grating; a transmissive diffraction grating, and, a prism.

26. The apparatus claimed in claim 25, wherein the dispersive element is a reflective concave diffraction grating.

27. The apparatus claimed in claim 25, wherein the dispersive element is positioned for dispersing light at each predetermined Wavelength along a dedicated secondary optical path.

28. The apparatus claimed in claim 27, wherein the dispersive element and the at least a light source are such that, in use, each predetermined wavelength of light of the plurality of different predetermined wavelengths of light, including the first predetermined wavelength of light and the second other predetermined wavelength of light, are from the ultraviolet-visible region of the electromagnetic spectrum.

29. The apparatus claimed in claim 28, wherein the at least a light source is for providing light at predetermined wavelengths of light that are approximately 230 nm, 250 nm, 280 nm, 300 nm, 320 nm, 350 nm, 400 nm and 450 nm.

30. The apparatus claimed in claim 29, wherein the at least a light source is selected from the group consisting of: a xenon arc lamp; a high powered deuterium lamp; and, a tungsten filament lamp.

31. The apparatus claimed in claim 30, wherein the channel detectors for detecting light at the predetermined wavelengths of approximately 250 nm, 300 nm, 350 nm, 400 nm and 450 nm optionally comprise:
   a band pass filter disposed between the target slit and the at least a light transmissive endface of the sample cell.

32. The apparatus claimed in claim 31, wherein the channel detectors for detecting light at the predetermined wavelengths of approximately 230 nm, 280 nm and 320 nm further comprise:
   a fold mirror disposed between the target slit and the at least a light transmissive endface of the sample cell; and
   a band pass filter optionally disposed between the fold mirror and the at least a light transmissive endface of the sample cell.

33. The apparatus claimed in claim 32, wherein the channel detectors for detecting light at the predetermined wavelengths of approximately 230 nm, 280 nm and 320 nm are disposed within a plane approximately normal to the plane containing the channel detectors for detecting light at the predetermined wavelengths of approximately 250 nm, 300 nm, 350 nm, 400 nm and 450 nm.

34. The apparatus claimed in claim 33, further comprising a fold mirror disposed within the initial optical path for directing light provided by the at least a light source onto the operational surface of the dispersive element.

* * * * *